United States Patent [19]

Muller et al.

[11] 4,407,955

[45] * Oct. 4, 1983

[54] FERMENTABLE SUGAR FROM THE HYDROLYSIS OF STARCH DERIVED FROM DRY MILLED CEREAL GRAINS

[75] Inventors: Werner C. Muller, Dobbs Ferry, N.Y.; Franklyn D. Miller, Cincinnati, Ohio

[73] Assignee: National Distillers and Chemical Corporation, New York, N.Y.

[*] Notice: The portion of the term of this patent subsequent to May 18, 1999 has been disclaimed.

[21] Appl. No.: 320,278

[22] Filed: Nov. 12, 1981

[51] Int. Cl.³ ............................ C13K 1/06; C12P 7/06
[52] U.S. Cl. ...................................... 435/161; 127/38; 127/40; 203/19; 203/DIG. 13
[58] Field of Search ...................... 127/37, 38, 39, 40; 435/161; 203/19, DIG. 13

[56] References Cited

U.S. PATENT DOCUMENTS 4,330,625  5/1982  Miller et al. ...................... 435/161

Primary Examiner—William F. Smith
Attorney, Agent, or Firm—Kenneth D. Tremain

[57] ABSTRACT

Starch derived from a dry milled cereal grain such as corn or milo is hydrolyzed to provide a sterile aqueous fermentable sugar solution which is especially adapted for fermentative conversion to ethanol with minimum thermal expenditure. Following a preliminary acid-catalyzed hydrolysis of the starch to provide a sterile hydrolysate slurry, the slurry is further hydrolyzed in the presence of added aqueous non-fermentable carbohydrate to reequilibrate the hydrolysis reaction in favor of increased production of fermentable sugar, primarily glucose. Substantially all of the water insoluble protein and oil components, and a portion of the water soluble components, e.g., sugars, proteins and vitamins, are separately recovered from the sterile hydrolysate either before or after the further hydrolysis step with the water solubles being recycled to the system to effect reequilibration of a further quantity of hydrolysate.

14 Claims, 1 Drawing Figure

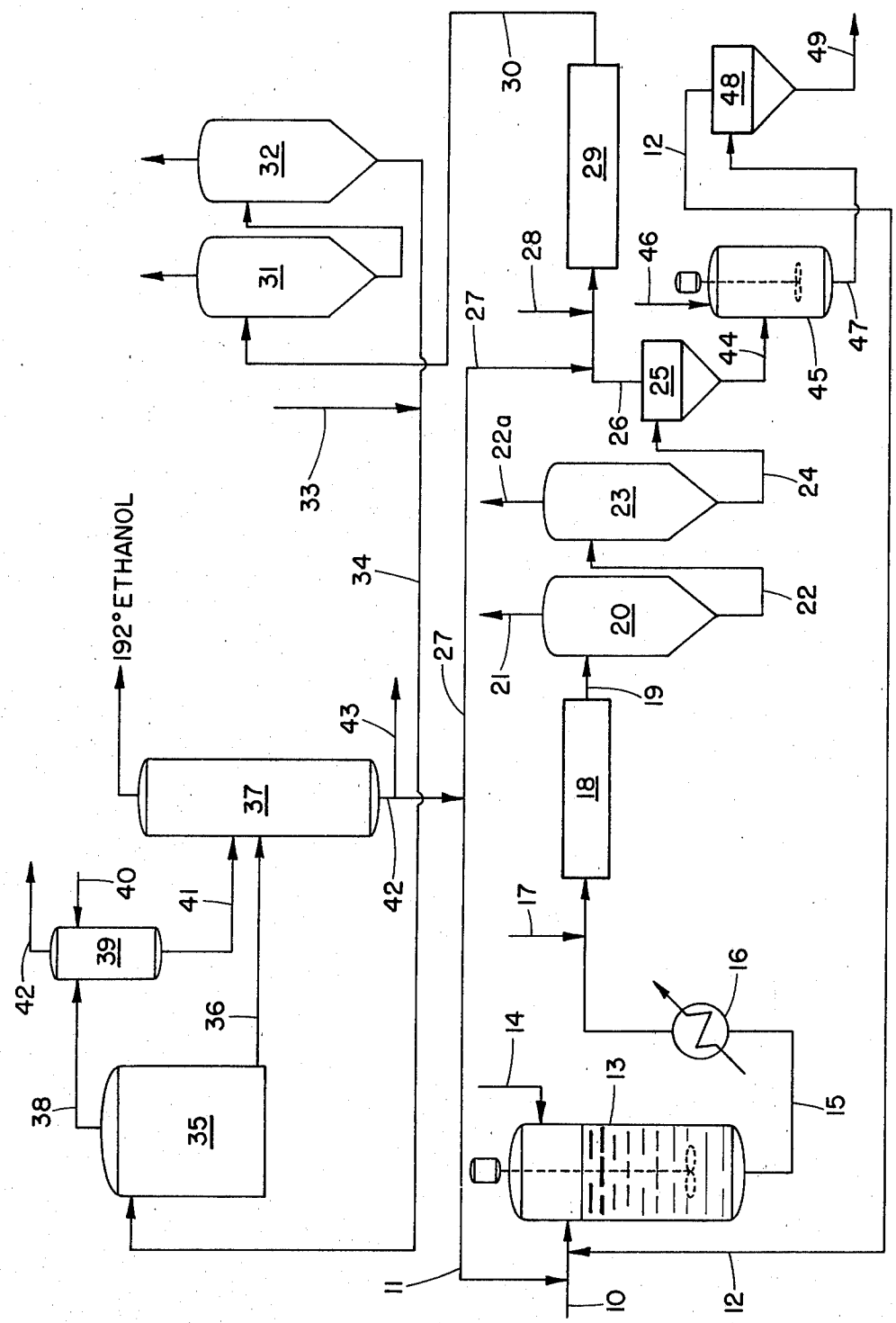

FERMENTABLE SUGAR FROM THE HYDROLYSIS OF STARCH DERIVED FROM DRY MILLED CEREAL GRAINS

REFERENCE TO RELATED APPLICATIONS

This application discloses subject matter which is disclosed and claimed in commonly assigned copending U.S. patent application Ser. Nos. 091,640 filed Nov. 5, 1979, now abandoned in favor of copending U.S. patent application Ser. No. 237,038, filed Feb. 23, 1981, 219,011 filed Dec. 22, 1980, now abandoned in favor of copending U.S. patent application Ser. No. 391,324 filed June 23, 1982, and U.S. patent application Ser. No. 320,277 filed Nov. 12, 1981 filed of even date herewith.

BACKGROUND OF THE INVENTION

This invention relates to the acid hydrolysis of starch derived from dry milled cereal grains such as corn and milo to provide fermentable sugar.

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity consumed and versatility in product synthesis.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentation of sugar to a dilute solution of ethanol ("beer") and the recovery of anhydrous ethanol by distillation, have been modified in numerous ways to achieve improvements in product yield, production rates and so forth (see, for example, U.S. Pat. No. 3,236,740 and the booklet "Industrial Alcohol by Continuous Fermentation and Vacuum Distillation With Low Energy Consumption", of Chemapec, Inc., Woodbury, N.Y.). For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol and enhance the standing of the ethanol as an economically viable replacement for petroleum based raw materials. To date, however, relatively little concern has been given to the energy and raw material requirements for manufacturing ethanol from biomass and consequently, little effort has been made to minimize the thermal expenditure and waste incurred in carrying out any of the aforesaid discrete operations involved in the manufacture of ethanol from vegetative sources.

Processes for the acid hydrolysis of carbohydrate polymers, i.e., starch and cellulose, to provide fermentable sugars are known (viz., U.S. Pat. Nos. 2,203,325; 2,210,659; 2,359,763; 2,393,095; 2,395,907; 2,529,131; 2,565,404; 2,946,706; 2,954,304; 2,989,425; 3,169,083; 3,200,012; 3,236,687; 3,313,654; 3,446,664; 3,484,287; 3,607,395; 4,137,094 and 4,155,884). While these and similar processes are for the most part readily adaptable to the hydrolysis of the finely divided, relatively pure starch derived from conventional processes of wet milling cereal grains, their application to the starch-containing fractions obtained from processes of dry milling cereal grains as currently practiced would be uneconomically wasteful of the protein and edible oil associated with these fractions which in the case of corn and milo, is especially significant. Wet milling processes typically remove all but an insignificant amount of non-starch materials, i.e., protein, cellulosic fiber and oil, from the starch component of the grain, the non-starch materials finding valuable application in their own right as animal feeds and feed supplements. However, from the standpoint of producing starch for conversion to sugar, the sugar to dilute ethanol and the dilute ethanol to essentially anhydrous ethanol, conventional wet-milling processes are undesirable because of the need to ultimately remove the large amounts of process water involved.

Where, as in the case of low cost industrial ethanol, a minimal use of energy is necessary to achieve an economically viable process, a relatively energy and capital intensive process such as one based on wet-milled corn starch as the starting material can be disadvantageous. For this reason, the hydrolytic conversion of starch derived from any of the known and conventional dry milling processes is especially desirable in an industrial scale anhydrous ethanol operation since dry milling processes employ no added water beyond the moisture which is already naturally present in the grain. Thus, for example, in a typical dry corn milling process, the kernels are broken by impact and the resulting fractions made up of grits and fine feed which contain the bulk of the starch and significant quantities of oil, protein, and cellulosic fiber, germ which contains most of the oil content of the kernels, and hulls which contain the major portion of the fiber, are separated employing degerminators, sifters, aspirators and gravity separators. A typical dry corn milling product analysis (pounds per bushel) is as follows:

| STREAM | ANALYSIS ON YELLOW CORN #2, LB/100 LB (DRY BASIS) | | | |
|---|---|---|---|---|
| | CORN | GERM | BRAN | GRITS |
| Starch | 34.27 | 1.33 | 1.14 | 31.80 |
| Protein | 4.28 | 0.64 | 0.27 | 3.37 |
| Oil | 2.05 | 1.05 | 0.17 | 0.83 |
| Fiber | 1.22 | 0.21 | 0.57 | 0.44 |
| Nitrogen-Free Extract | 5.00 | 0.21 | 0.15 | 0.41 |
| Ash | 0.77 | 1.32 | 1.50 | 2.18 |
| Dry Solids | 47.59 | 4.76 | 3.80 | 39.03 |
| Moisture | 8.41 | 0.84 | 0.68 | 6.89 |
| TOTAL | 56.00 | 5.60 | 4.48 | 45.92 |

As this analysis indicates, the grits contain 92.8% of the starch, 78.7% of the protein and 40.5% of the oil of the whole corn kernels. Direct complete hydrolysis of the grits would therefore make these substantial amounts of protein and oil unavailable for use as comestibles.

Accordingly, there has heretofore existed a need for a process for converting starch derived from dry milled cereal grains to fermentable sugars while recovering substantially all of the protein and oil content of the starch component of the dry milled grain prior to the complete hydrolysis of the starch. The term "cereal grain" as used herein is to be understood in its commonly used sense and is inclusive of all varieties of corn (maize), milo, wheat, rice, and the like.

In addition to the foregoing consideration, it is known that besides the desired reaction whereby the carbohydrate polymer molecules are split into frementable sugars, other reactions taking place during hydrolysis tend to reduce the maximum theoretical conversion of available carbohydrate to such sugars and produce non-fermentable hydrolysate product. Three of the principal types of undesirable reactions known to take place in acid catalyzed carbohydrate polymer hydrolysis are: degradation (starch molecule is irreversibly destroyed to provide 5-hydroxymethylfurfural which hydrolyzes to levulinic acid and formic acid, and separately to humins); reversion (glucose repolymerizes and/or isomerizes to unfermentable substances); and retrogradation (hydrolysis splits out the branched chain components of the starch molecule leaving a straight chain, lower molecular weight water insoluble polymeric molecule which crystallizes at about 70°–80° C. and becomes resistant to further hydrolysis). In a typical acid hydrolysis process, when equilibrium has been achieved, from about 15 to about 20 weight percent of the depolymerized starch will be present in the form of one or more of the foregoing non-fermentable hydrolysates, the balance of the depolymerized starch being present as glucose and/or other fermentable sugar(s). To the extent non-fermentable products are produced side-by-side with fermentable sugar(s), they represent a loss in yield of the hydrolysis reaction and compromise the usefulness of acid hydrolysis as a process for obtaining fermentable sugar on a large-scale, economical basis.

According to U.S. Pat. No. 2,529,121 referred to supra, the non-fermentable hydrolysate products resulting from one or more of the aforesaid undesirable reactions eventually is recovered in the stillage, or "vinnasse", obtained as a result of the distillation of the dilute ethanol, or "beer", resulting from the fermentation of the fermentable sugar portion of the hydrolysate. To maximize overall ethanol production based on the original quantity of carbohydrate polymer employed, it is proposed in U.S. Pat. No. 2,529,131 to subject the stillage to further acid hydrolysis to convert the unfermentable products therein to fermentable sugars.

SUMMARY OF THE INVENTION

In accordance with the present invention, a process is provided for converting starch derived from dry milled whole grain, which starch contains varying amounts of water insoluble protein and oil depending upon the nature of the grain, and which are relatively substantial in the case of corn and milo, and relatively small amounts of one or more water soluble components selected from the group consisting of sugar, protein, vitamin and mineral, to fermentable sugar to provide substrate for the thermally efficient large-scale production of ethanol. U.S. patent application Ser. No. 219,011, filed Dec. 22, 1980, now abandoned in favor of copending U.S. patent application Ser. No. 391,324 filed June 23, 1982, which is incorporated by reference herein describes a dry milling process which is especially advantageous for use in the present invention. An aqueous slurry of the dry milled starch, preferably one which has been prepared with stillage obtained from an ethanol concentration facility and/or repulp supernatant as hereinafter described, is subjected to a preliminary acid catalyzed hydrolysis, advantageously in accordance with the process described in Ser. No. 091,640, filed Nov. 5, 1979, now abandoned in favor of copending U.S. patent application Ser. No. 237,038, filed Feb. 23, 1981, which is incorporated by reference herein (employing, inter alia, elevated pressure and temperature), to provide a sterile partial hydrolysate. This partial hydrolysate, which contains a water insoluble phase made up of water insoluble protein and oil and a water soluble phase made up of fermentable sugars, partial hydrolysates and other water soluble components of the starch, is then preferably subjected to a partial pressure and temperature reduction with the steam thus generated advantageously being used in some other capacity in the process, e.g., to preheat water, stillage and/or repulp supernatant used in preparing the aqueous starch slurry. As a result of the aforesaid preliminary hydrolysis step, the proteins originally present in the starch undergo modification thereby facilitating their later separation and recovery from the hydrolysate by centrifugation. The partial hydrolysate, optionally at reduced pressure and temperature, is thereafter subjected to a further and final hydrolysis in the presence of aqueous water soluble non-fermentable carbohydrate, e.g., any of the degradation, reversion and/or retrogradation products referred to above, whereby a sterile, substantially fully hydrolyzed starch slurry of high fermentable sugar content is obtained. The presence of aqueous water soluble non-fermentable carbohydrate (which is recovered as stillage and/or as repulped supernatant from the conversion of a previous quantity of starch to concentrated ethanol) at the commencement of the final hydrolysis step provides several very significant advantages each of which results in a greater overall production of fermentable sugar when a steady-state process has been achieved. For one, the presence of non-fermentable carbohydrate during final hydrolysis reequilibrates the hydrolysate with the result that higher conversion levels of partial hydrolysate to fermentable sugar are obtained. For another, the addition of more water (the solvent medium for the non-fermentable carbohydrate) to the partial hydrolysate lowers its solids content whereby the equilibrium of the final hydrolysis reaction is shifted still further to the production of fermentable sugar. Following final hydrolysis, the starch hydrolysate is preferably subjected to further pressure and temperature reduction, the generated steam values likewise advantageously being used in some other useful capacity. The sterile hydrolysate slurry is then separated into an aqueous portion containing fermentable sugars, primarily glucose, and a part of the water soluble components and a water insoluble protein and oil (and fiber, if originally present) portion containing the remaining part of the water soluble components. The aforesaid aqueous solution of fermentable sugar, following neutralization of the acid therein with a base such as ammonia, alkali metal hydroxide, alkaline earth metal hydroxide, or the like, is then conveyed to a fermentation unit where conversion of the sugar to ethanol and further hydrolysis of any partial starch hydrolysate present therein to fermentable sugar takes place (when saccharifying enzyme is present). It is also within the scope of this invention to remove the protein, oil and/or fiber from the partial hydrolysate prior to subjecting the latter to final hydrolysis.

The previously separated water insoluble protein and oil portion may be diluted or repulped with water or stillage to dissolve the water soluble components associated therewith with the resulting aqueous slurry thereafter being separated into a protein and oil portion substantially free of any of the water soluble components of the original starch and starch hydrolysate, and an aqueous portion containing most of the water soluble components. The protein and oil may be used directly in animal feed or, if desired, they may be separately recovered for individual use. The aqueous portion containing water soluble components of the starch, i.e., repulped supernatant, is advantageously recycled for use in the aforedescribed final hydrolysis step.

Employing the foregoing starch hydrolysis process, only minimal quantities of fresh water need be used to accomplish conversion of the starch to fermentable sugar thus reducing the amount of water which must be removed from product ethanol obtained from the fermentation of the sugar, and consequently, the amount of thermal energy which must be expended in the manufacture of the ethanol. Since substantially all of the water insoluble protein contained in the original starch can be recovered for other commercially valuable uses, notably animal feed, and due to the water recycle feature which is made possible by the process herein, a good portion of the water soluble components of the starch are retained in the solution of product fermentable sugar and are therefore available for satisfying certain nutrient requirements of the yeast employed in the fermentation of the sugar to ethanol.

BRIEF DESCRIPTION OF THE DRAWING

The accompanying drawing is a diagrammatic flow sheet illustrative of the starch hydrolysis process of the present invention as applied to conventionally dry milled, dehulled, degerminated corn grits which, as shown above, contains the major amount (i.e., typically over 93%) of the starch originally present in the whole corn, together with lesser quantities of protein, oil and fiber. The process contemplates the use of known and conventional equipment which is readily available from several suppliers.

DESCRIPTION OF THE PREFERRED EMBODIMENTS

Referring to the drawing, dry milled corn grits at ambient temperature and pressure passing through line 10 is slurried with water, preferably in the form of stillage flowing through line 11 and/or repulp supernatant flowing through line 12, into stirred starch slurry tank 13. An aqueous solution of sulfuric acid (98% acid by weight) is introduced into starch slurry tank 13 through line 14. Good results can be achieved with other acids, e.g., hydrochloric, phosphoric, nitric, etc., in amounts sufficient to provide an acidified starch slurry having a pH of from about 1.0 to about 2.5. Stillage is available in generous quantities from the ethanol distillation operation and repulp supernatant is provided as a result of the protein and oil separation procedures hereinafter more fully described. While the amount of water added to the grits can vary widely, it is preferred to use only so much water as is necessary to achieve a pumpable slurry so as to minimize the amounts of water which must later be removed in the downstream fermentation ethanol concentration facility. Slurries containing from about 20% to about 50% starch, and preferably from about 30% to about 40% starch (dry solids), by weight of the entire slurry are generally readily manageable by most conventional pumping equipment. Following the slurrying operation, the acidified aqueous slurry of starch passing through line 15 is pressurized and raised to a temperature of about 75° C. by heater 16 and thereafter mixed with high pressure steam introduced through line 17. Hydrolysis of the starch to partial hydrolysate and some fermentable sugar thereafter occurs in preliminary hydrolysis unit 18. The pressure imparted to the starch slurry can vary over fairly wide limits but in any event must be a pressure which is in excess of the saturation pressure of water at the temperature of the hydrolysate stream passing through line 19, preferably by at least about 50 psig. Pressures on the order of from about 100 to about 1,000 psig and advantageously, from about 600 to about 900 psig, generally provide good results. The amount of steam delivered to the starch slurry through line 17 should be sufficient to increase the temperature of the slurry to within the range of from about 140° C. to about 220° C. and preferably from about 160° C. to about 200° C. Residence time of the starch slurry in hydrolysis unit 18 to effect substantial hydrolysis and sterilization of the starch is not a critical consideration. In general, residence times of just a few seconds, e.g., from about 5–10 seconds, to 10 minutes or more, provide good results. Under the foregoing conditions of hydrolysis, the accompanying water insoluble protein will undergo modification facilitating its efficient recovery by such conventional means as centrifugation. The hydrolyzed starch slurry is then conveyed through line 19 to a first optional pressure reduction vessel 20 in which a partial pressure reduction takes place to partially cool the slurry for the subsequent equilibration step. In the embodiment of the process shown in the drawing, steam generated by the foregoing partial pressure reduction operation recovered through line 21 is advantageously passed through a heat exchanger to pre-heat the stillage and/or the repulp supernatant streams.

The cooled, partially depressurized slurry is then conveyed through line 22 to an optional second pressure reduction vessel 23 where the pressure is let down further, advantageously to atmospheric level. Generated steam recovered through line 22a is likewise utilized in some other useful capacity. The depressurized slurry emerging from vessel 23 through line 24 is introduced into a first separator unit 25, preferably a centrifuge, with the sterile aqueous fermentable sugar supernatant recovered therefrom through line 26 being mixed with stillage flowing through line 27 and optionally with high pressure steam through line 28 prior to introduction into final hydrolysis unit 29. Quantities of steam and operating pressures of final hydrolysis unit 29 can, if desired, be similar to those previously described in connection with the operation of preliminary hydrolysis unit 18. Alternatively or in addition to stillage, the supernatant in line 26 can be mixed with repulp supernatant flowing through line 12. The amount of stillage/repulp supernatant added to the initial hydrolysate can vary widely but in general, will be an amount which, because of the reequilibrating effect of the non-fermentable carbohydrate therein, will result in the production of significantly greater quantities of fermentable sugar, mostly glucose, than would be obtained in the absence of stillage/repulp supernatant. Thus, instead of a final dextrose equivalent (D.E.) of about 75-80 which would result from a conventional acid hydrolysis process, the addition herein of stillage/repulp supernatant in final hydrolysis unit 29 results in a significant increase in D.E. levels, e.g., from about 85 to 95 and even higher. Emerging from final hydrolysis unit 29 through line 30, the hydrolysate or "sugar liquor" is depressurized as required in a series of pressure reduction units 31 and 32 which operate substantially in the same manner as pressure reduction units 20 and 23. The hydrolysate emerging from pressure reduction unit 32, now at its maximum fermentable sugar content for the conditions chosen, is combined with an amount of base, e.g., ammonia or ammonium hydroxide, supplied through line 33 to reduce the pH of the hydrolysate to a level suitable for optimum fermentation, e.g., to about pH 4.0, and the neutralized hydrolysate is then passed through line 34 into fermentation unit 35 for conversion of the sugar to ethanol. When the salt resulting from neutralization of the acid is recycled (as will be the case when stillage and/or repulped supernatant is added to the starch slurry/partial starch hydrolysate), a buffering action results so that it becomes necessary to add still higher levels of acid to achieve a pH which is appropriate for hydrolysis. Such higher levels of acid eventually result in the production of still more salt which results in an even greater buffering action. Accordingly, it may be advantageous to contact the stillage and/or repulp supernatant with a strong acid cation exchange resin, e.g., Dow's Dowex MWA-1 and XFS-4066 which are copolymers of styrene and divinylbenzene with controlled crosslinkage, in order to remove cations, e.g., $NH_4^+$, and regenerate acid. Dilute aqueous ethanol resulting from fermentation is introduced through line 36 into a rectifier column 37 for concentration to high proof, e.g., 192° ethanol. The ethanol-containing carbon dioxide vapor produced in fermentation unit 35 is advantageously passed through line 38 to stripper column 39 fed with cold water through line 40. The water passing downwardly through the stripper absorbs most of the ethanol present in the incoming aqueous stream and the resulting aqueous stream is introduced into rectifier column 37 through line 41, carbon dioxide being discharged from the scrubber through line 42. Stillage from the rectifier column is recovered therefrom through line 42 with part being purged through line 43 as required. The remaining stillage may then be divided into streams 11 for slurrying corn grits and/or line 27 for use in hydrolysis as previously described. The underflow, or "mud", recovered from separator unit 25 through line 44 is repulped with water, preferably stillage, supplied through line 46 in repulp vessel 45 and the repulped liquid, containing oil, water insoluble protein and some water soluble components, is introduced through line 47 into a second separator unit 48, preferably a centrifuge, with the repulp supernatant (i.e., the water soluble component(s)-containing phase) flowing through line 12 being optionally combined with stillage flowing through line 11, the combined streams thereafter being used in the slurrying operation and/or hydrolysis steps as previously described. The underflow, or "mud", recovered from separator 48 is discharged through line 49. This mud contains all of the protein and oil, together with residual quantities of carbohydrates, present in the original corn grits and as such constitutes (when dried) a nutritious animal feed or feed supplement.

The following represents a material balance (lb/hr) for various stages of the process herein.

| ACID HYDROLYSIS OF CORN GRITS TO PROVIDE STERILE AQUEOUS FERMENTABLE SUGAR AND PROTEIN/OIL BY-PRODUCT | | | | | |
|---|---|---|---|---|---|
| | STREAM (Corresponding to the Drawing) | | | | |
| COMPONENT | 10 | 27 | 12 | (Prior to Mixture 15 with Steam) | (After Mixture 15 with Steam) |
| Water/Steam | 18,259.00 | 130,617.31 | 64,420.43 | 182,079.19 | 308,949.50 |
| Ethanol | — | 44.86 | 2.24 | 36.59 | 36.59 |
| Glycerol | — | 15,167.17 | 756.79 | 12,374.00 | 12,374.00 |
| Starch | 84,270.00 | — | — | 84,269.87 | 84,269.87 |
| Fermentable Sugar | — | 93.54 | 3,413.55 | 3,485.17 | 3,485.17 |
| Non-Fermentable Sugar | 3,763.00 | 9,573.36 | 3,413.55 | 14,506.44 | 14,506.44 |
| Protein | 12,297.00 | 376.83 | 73.92 | 12,659.42 | 12,659.42 |
| Extractables | 3,101.00 | 12,935.44 | 847.45 | 13,856.18 | 13,856.18 |
| Sulfuric Acid | — | — | 178.75 | 178.75 | 2,922.58 |
| Ammonia | — | — | — | — | — |
| Ammonium Sulfate | — | 15,393.57 | 768.27 | 12,561.95 | 12,561.99 |
| Live Yeast | — | — | — | — | — |
| Dead Yeast | — | 884.63 | 44.14 | 721.76 | 721.76 |
| Vitamins | — | 0.04 | — | 0.04 | 0.04 |
| Carbon Dioxide | — | 0.01 | — | 0.01 | 0.01 |
| TOTAL | 121,690.00 | 185,086.50 | 73,918.94 | 337,329.06 | 466,343.19 |

| ACID HYDROLYSIS OF CORN GRITS TO PROVIDE STERILE AQUEOUS FERMENTABLE SUGAR AND PROTEIN/OIL BY-PRODUCT | | | | |
|---|---|---|---|---|
| | STREAM (Corresponding to the Drawing) | | | |
| COMPONENT | 19 | 21 | 24 | 44 |
| Water/Steam | 299,587.12 | 50,734.82 | 248,852.25 | 22,775.59 |
| Ethanol | 36.59 | — | 36.59 | 3.35 |
| Glycerol | 12,374.00 | — | 12,374.00 | 1,132.50 |
| Starch | 0.06 | — | 0.06 | 0.01 |
| Fermentable Sugar | 55,811.87 | — | 55,811.87 | 5,108.05 |
| Non-Fermentable Sugar | 55,811.87 | — | 55,811.87 | 5,108.05 |
| Protein | 12,659.42 | — | 12,659.42 | 12,292.97 |
| Extractables | 13,856.18 | — | 13,856.18 | 1,268.15 |
| Sulfuric Acid | 2,922.58 | — | 2,922.58 | 267.48 |
| Ammonia | — | — | — | — |
| Ammonium Sulfate | 12,561.99 | — | 12,561.99 | 1,149.71 |
| Live Yeast | — | — | — | — |
| Dead Yeast | 721.76 | — | 721.76 | 66.06 |

-continued

ACID HYDROLYSIS OF CORN GRITS
TO PROVIDE STERILE
AQUEOUS FERMENTABLE SUGAR AND
PROTEIN/OIL BY-PRODUCT

| | STREAM (Corresponding to the Drawing) | | | |
|---|---|---|---|---|
| COMPONENT | 19 | 21 | 24 | 44 |
| Vitamins | 0.04 | — | 0.04 | — |
| Carbon Dioxide | 0.01 | — | 0.01 | — |
| TOTAL | 466,343.12 | 50,734.82 | 415,608.25 | 49,171.89 |

ACID HYDROLYSIS OF CORN GRITS TO PROVIDE STERILE
AQUEOUS FERMENTABLE SUGAR AND PROTEIN/OIL BY-PRODUCT

| | STREAM (Corresponding to the Drawing) | | | | |
|---|---|---|---|---|---|
| COMPONENT | 46 | 47 | 49 | (Prior to Mixture with Stillage 26 and Steam) | (After Mixture with Stillage 26 and Steam) |
| Water/Steam | 73,632.56 | 96,399.12 | 31,978.71 | 226,076.50 | 356,693.94 |
| Ethanol | — | 3.35 | 1.11 | 33.24 | 78.11 |
| Glycerol | — | 1,132.50 | 375.69 | 11,241.49 | 26,408.66 |
| Starch | — | 0.01 | — | 0.06 | 0.07 |
| Fermentable Sugar | — | 5,108.05 | 1,694.50 | 50,703.82 | 50,797.36 |
| Non-Fermentable Sugar | — | 5,108.05 | 1,964.50 | 50,703.82 | 60,277.19 |
| Protein | — | 12,292.97 | 12,219.03 | 366.44 | 743.27 |
| Extractables | — | 1,268.15 | 420.69 | 12,588.03 | 25,523.48 |
| Sulfuric Acid | — | 267.48 | 88.73 | 2,655.10 | 2,655.10 |
| Ammonia | — | — | — | — | — |
| Ammonium Sulfate | — | 1,149.71 | 381.39 | 11,412.27 | 26,805.85 |
| Live Yeast | — | — | — | — | — |
| Dead Yeast | — | 66.06 | 21.91 | 655.70 | 1,540.33 |
| Vitamins | — | — | — | 0.03 | 0.08 |
| Carbon Dioxide | — | — | — | 0.01 | 0.02 |
| TOTAL | 73,623.56 | 122,795.06 | 48,876.26 | 366,436.12 | 551,523.12 |

ACID HYDROLYSIS OF CORN GRITS
TO PROVIDE STERILE
AQUEOUS FERMENTABLE SUGAR AND
PROTEIN/OIL BY-PRODUCT

| | STREAM (Corresponding to the Drawing) | | | |
|---|---|---|---|---|
| COMPONENT | 30 | 33 | 34 | 11 |
| Water/Steam | 356,693.87 | — | 261,516.87 | 100,000.00 |
| Ethanol | 78.11 | — | 78.11 | 34.35 |
| Glycerol | 26,408.66 | — | 26,408.66 | 11,617.23 |
| Starch | — | — | — | — |
| Fermentable Sugar | 92,191.81 | — | 92,191.81 | 71.62 |
| Non-Fermentable Sugar | 18,882.62 | — | 18,882.62 | 7,329.91 |
| Protein | 743.27 | — | 743.27 | 288.52 |
| Extractables | 25,523.48 | — | 25,523.48 | 9,907.76 |
| Sulfuric Acid | 2,655.10 | — | 2,655,10 | — |
| Ammonia | — | 921.05 | 921.05 | — |
| Ammonium Sulfate | 26,805.85 | — | 26,805.85 | 11,793.74 |
| Live Yeast | — | — | — | — |
| Dead Yeast | 1,540.33 | — | 1,540.33 | 677.62 |
| Vitamins | 0.08 | — | 0.08 | 0.03 |
| Carbon Dioxide | 0.02 | — | 0.02 | 0.01 |
| TOTAL | 551,552.94 | 921.05 | 457,266.94 | 141,720.44 |

What is claimed is:

1. A process for converting the starch fraction derived from whole dry milled cereal grain to a sterile aqueous solution of fermentable sugar, said starch containing water insoluble protein and oil, which comprises:

(a) hydrolyzing in a preliminary hydrolysis step an aqueous slurry of the starch in the presence of an acid hydrolysis catalyst at an elevated pressure and temperature to provide a starch hydrolysate slurry containing water insoluble protein and oil and water soluble components;

(b) separating water insoluble protein and oil with or without water soluble components from the hydrolysate resulting from step (a); and, (c) hydrolyzing in a further hydrolysis step the aqueous sterile starch hydrolysate slurry resulting from step (a) in the presence of added aqueous water soluble non-fermentable carbohydrate to provide a sterile aqueous solution of fermentable sugar.

2. A process for converting the starch fraction derived from whole dry milled cereal grain to a sterile aqueous solution of fermentable sugar, said starch containing water insoluble protein and oil, which comprises:

(a) hydrolyzing in a preliminary hydrolysis step an aqueous slurry of the starch in the presence of an acid hydrolysis catalyst at an elevated pressure and temperature to provide a starch hydrolysate slurry containing water insoluble protein and oil and water soluble components;

(b) hydrolyzing in a further hydrolysis step the aqueous sterile starch hydrolysate slurry resulting from step (a) in the presence of added aqueous water soluble non-fermentable carbohydrate to provide a sterile aqueous solution of fermentable sugar; and (c) separating water insoluble protein and oil with or without water soluble components from the hydrolysate resulting from step (b).

3. The process of claim 1 or 2 wherein step (c) is carried out at an elevated pressure and temperature which is less than the pressure and temperature of step (a).

4. The process of claim 1 or 2 wherein the cereal grain feed for hydrolyzing step (a) is corn or milo.

5. The process of claim 1 or 2 wherein the cereal grain feed for hydrolyzing step (a) is dehulled corn or milo.

6. The process of claim 1 or 2 wherein the cereal grain feed for hydrolyzing step (a) is degerminated corn or milo.

7. The process of claim 1 or 2 wherein the sterile aqueous solution of fermentable sugar is subjected to fermentation to provide dilute aqueous ethanol.

8. The process of claim 7 wherein the concentrated ethanol is substantially dehydrated to provide anhydrous ethanol.

9. The process of claim 1 or 2 further comprising the steps of:

(d) diluting the water insoluble protein and oil resulting from step (c) with water;

(e) separating water from the water insoluble protein and oil resulting from step (d); and, (f) recycling the water recovered in step (e) as a source of water soluble carbohydrate for use in hydrolysis step (c) and/or for preparing the starch slurry for hydrolysis step (a).

10. The process of claim 9 wherein the dilution water in step (b) is stillage from an ethanol concentration facility.

11. The process of claim 1 or 2 wherein the aqueous slurry of starch is prepared with stillage from an ethanol concentration facility.

12. The process of claim 1 or 2 wherein stillage from an ethanol concentration facility is used as a source of water soluble non-fermentable carbohydrate for use in hydrolysis step (c).

13. The process of claim 9 wherein the stillage is contacted with an ion exchange resin prior to use in forming the starch slurry.

14. The process of claim 10 wherein the stillage is contacted with an ion exchange resin prior to use in hydrolysis step (c).

* * * * *